United States Patent [19]
Mori et al.

[11] Patent Number: 5,948,636
[45] Date of Patent: Sep. 7, 1999

[54] DNA AND HOST CELLS ENCODING A CELL SURFACE PROTEIN OF PORPHYROMONAS GINGIVALIS

[75] Inventors: Hideharu Mori, Suntou-gun; Mamoru Hasegawa, Matsudo; Masanori Fukui, Himeji; Kenji Yasuda; Keiko Yamada, both of Ogaki; Shusaburo Hokukoku, Kani; Tomohiko Ogawa, Toyonaka, all of Japan

[73] Assignees: Kyowa Hakko Kogyo Co., Ltd.; Kyowa Medex Co., Ltd., both of Tokyo, Japan; Meito Sangyo Kabushiki Kaisha, Aichi, Japan

[21] Appl. No.: 08/714,168
[22] PCT Filed: Mar. 29, 1995
[86] PCT No.: PCT/JP95/00584
    § 371 Date: Nov. 22, 1996
    § 102(e) Date: Nov. 22, 1996
[87] PCT Pub. No.: WO95/26404
    PCT Pub. Date: Oct. 5, 1995

[30] Foreign Application Priority Data

Mar. 29, 1994 [JP] Japan .................................. 6-081074
Jul. 8, 1994 [JP] Japan .................................. 6-180815

[51] Int. Cl.⁶ .............................. C12N 1/21; C12N 5/31; C12N 15/63; C07K 14/195
[52] U.S. Cl. .................. 435/69.1; 435/243; 435/252.33; 435/320.1; 536/23.1; 536/23.7; 530/820; 530/825
[58] Field of Search .................................... 530/350, 69.1, 530/243, 252.33, 320.1, 820, 825; 536/23.1, 23.7

[56] References Cited

PUBLICATIONS

T. Ogawa et al., "Molecular Cloning and Characterization of the Genes Encoding the Immunoreactive Major Cell–Surface Proteins of *Porphyromonas gingivalis*", FEMS Micro-biology Letters, vol. 120, No. 1–2, pp. 23–30, 1994.

K. Watanabe et al., "Molecular Cloning and Expression of a Major Surface Protein (the 75–kDa protein) of *Porphyromonas* (Bacteroides) *gingivalis* in *Escherichia coli*", FEMS Microbiology Letters, vol. 92, No. 1, pp. 47–56, 1992.

R. T. Evans et al., "Immunization with *Porphyromonas* (Bacteroides) *gingivalis* Fimbriae Protects against Periodontal Destruction", Infection and Immunity, vol. 60, No. 7, pp. 2926–2935, Jul. 1992.

*Primary Examiner*—John Ulm
*Assistant Examiner*—Christine Saoud
*Attorney, Agent, or Firm*—Wenderoth, Lind & Ponack, L.L.P.

[57] ABSTRACT

A DNA encoding a cell surface polypeptide of *Porphyromonas gingivalis*, and a recombinant DNA being a DNA having integrated the encoding DNA thereinto. The cell surface polypeptide of the periodontopathic organism useful for prophylaxis and diagnosis of periodontal diseases can be obtained in a large amount by a microorganism containing the recombinant DNA wherein the DNA was integrated.

15 Claims, 1 Drawing Sheet

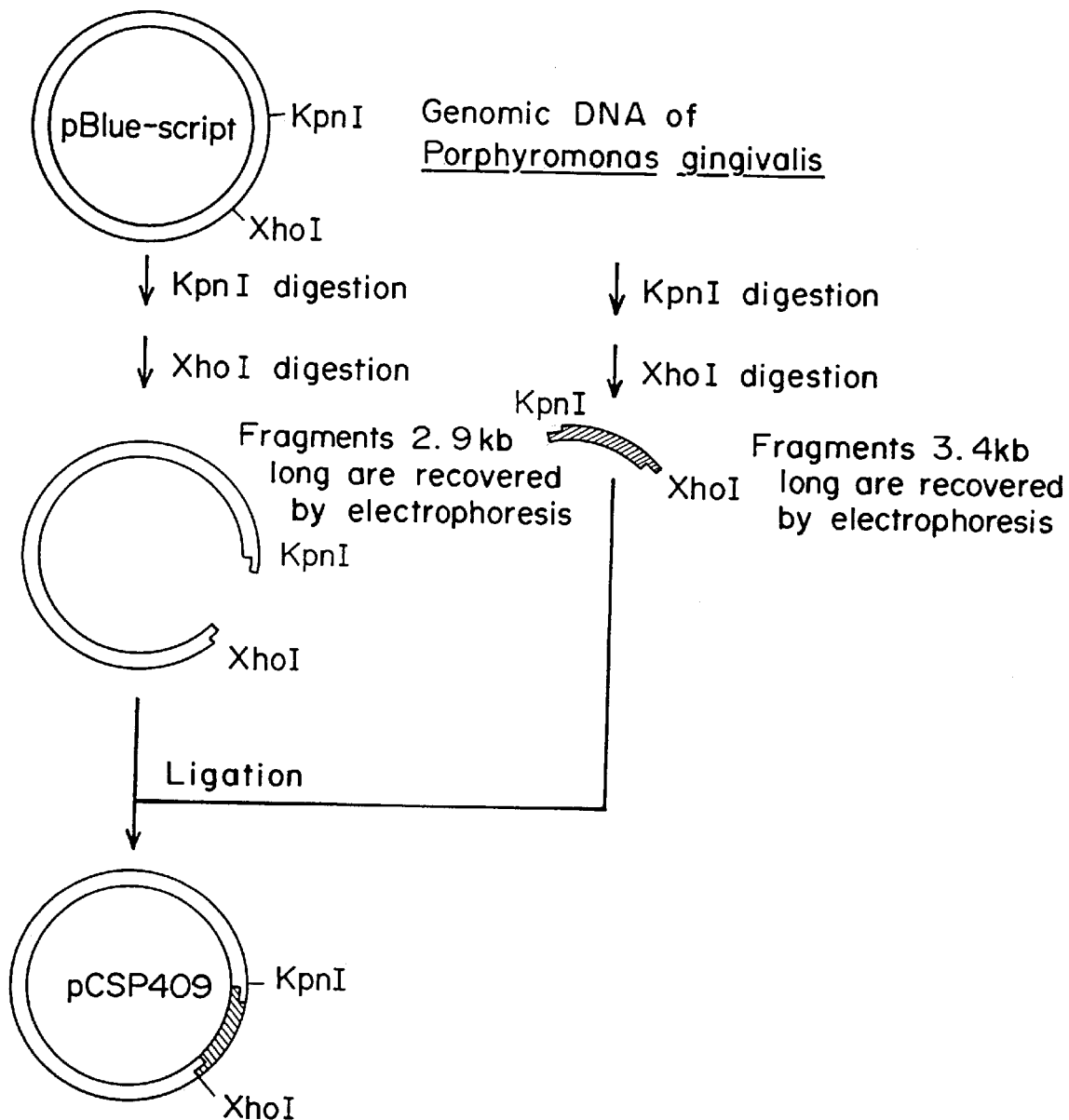

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
        (A) LENGTH: 563 amino acid
        (B) TYPE: amino acid
        (C) STRANDEDNESS: single
        (D) TOPOLOGY: linear (ii) MOLECULE TYPE:

(vi) ORIGINAL SOURCE:
        (A) ORGANISM: Porphyromonas (Bacteroides) gingivalis
        (B) STRAIN: OMZ409

(xi) SEQUENCE DESCRIPTION: SEQ ID NO:1:

```
Met Lys Leu Asn Lys Met Phe Leu Val Gly Ala Leu Leu Ser Leu Gly
 -5               1               5                   10

Phe Ala Ser Cys Ser Lys Glu Gly Asn Gly Pro Asp Pro Asp Asn Ala
            15                  20                  25

Ala Lys Ser Tyr Met Ser Met Thr Leu Ser Met Pro Met Gly Ser Ala
            30                  35                  40

Arg Ala Gly Asp Gly Gln Asp Gln Ala Asn Pro Asp Tyr His Tyr Val
    45                  50                  55

Gly Glu Trp Ala Gly Lys Asp Lys Ile Glu Lys Val Ser Ile Tyr Met
 60                  65                  70                  75

Val Pro Gln Gly Gly Pro Gly Leu Val Glu Ser Ala Glu Asp Leu Asp
                80                  85                  90

Phe Gly Thr Tyr Tyr Glu Asn Pro Thr Ile Asp Pro Ala Thr His Asn
                95                 100                 105

Ala Ile Leu Lys Pro Lys Lys Gly Ile Lys Val Asn Ser Ala Val Gly
            110                 115                 120

Lys Thr Val Lys Val Tyr Val Val Leu Asn Asp Ile Ala Gly Lys Ala
    125                 130                 135

Lys Ala Leu Leu Ala Asn Val Asn Ala Ala Asp Phe Asp Ala Lys Phe
    140                 145                 150                 155

Lys Glu Val Ile Glu Leu Ser Thr Gln Ala Gln Ala Leu Gly Thr Val
                160                 165                 170

Ala Asp Gly Pro Asn Pro Ala Thr Ala Ala Gly Lys Ile Ala Lys Lys
            175                 180                 185

Asn Gly Thr Thr Asp Glu Thr Ile Met Met Thr Cys Leu Gln Pro Ser
            190                 195                 200
```

-continued

```
Asp Ala Leu Thr Ile Glu Ala Val Ser Glu Ala Asn Ala Ile Ala
    205                 210                 215
Gly Ile Lys Asn Gln Ala Lys Val Thr Val Glu Arg Ser Val Ala Arg
    220                 225                 230                 235
Ala Met Val Ser Thr Lys Ala Gln Ser Tyr Glu Ile Lys Ala Thr Thr
                240                 245                 250
Gln Ile Gly Glu Ile Ala Ala Gly Ser Val Leu Ala Thr Ile Thr Asp
                255                 260                 265
Ile Arg Trp Val Val Ala Gln Gly Glu Arg Arg Gln Tyr Leu Ser Lys
            270                 275                 280
Lys Arg Gly Thr Val Pro Glu Asn Thr Trp Val Thr Pro Gly Ser Gly
            285                 290                 295
Phe Val Pro Thr Ser Ser Thr Phe His Thr Asn Ala Thr Glu Tyr Tyr
300                 305                 310                 315
Asp Tyr Ala Gly Leu Trp Glu Asp His Asn Thr Asn Glu Ala Val Ile
                320                 325                 330
Ser Gly Thr Gln Val Pro Thr Leu Ala Asp Tyr Gln Leu Gln Asp Val
                335                 340                 345
Thr Gly Glu Leu Ala Asn Ala Leu Ser Gly Lys Phe Leu Leu Pro Asn
                350                 355                 360
Thr His Lys Ser Gly Ala Asn Ala Ala Ser Ser Asp Tyr Lys Arg Gly
    365                 370                 375
Asn Thr Ala Tyr Val Leu Val Arg Ala Lys Phe Thr Pro Lys Lys Glu
380                 385                 390                 395
Ala Phe Ile Asp Arg Gly Lys Thr Tyr Ser Asp Asn Thr Ala Val Pro
                400                 405                 410
Glu Tyr Val Ala Gly Glu Asp Phe Phe Val Gly Glu Asn Gly Gln Phe
                415                 420                 425
Tyr Val Ser Met Lys Ser Val Thr Asp Pro Lys Val Gly Val Ala
                430                 435                 440
Gly Met Lys Ala His Lys Tyr Val Lys Gly Lys Val Leu Tyr Tyr Ala
    445                 450                 455
Trp Leu Asn Pro Ser Thr Thr Ser Pro Asp Ser Trp Trp Asn Ser Pro
460                 465                 470                 475
Val Val Arg Asn Asn Ile Tyr His Ile His Ile Lys Ser Ile Lys Lys
                480                 485                 490
Leu Gly Phe Asn Trp Asn Pro Leu Val Pro Asp Pro Asp Pro Ser Asn
            495                 500                 505
Pro Glu Asn Pro Asn Asn Pro Asp Pro Asn Pro Asp Glu Pro Gly Thr
        510                 515                 520
Pro Val Pro Thr Asp Pro Glu Gln Pro Leu Pro Asp Gln Asp Thr Phe
    525                 530                 535
Met Ser Val Glu Val Thr Val Leu Pro Trp Lys Val His Ser Tyr Glu
540                 545                 550                 555
Val Asp Leu
        558

(2) INFORMATION FOR SEQ ID NO:2:

(i) SEQUENCE CHARACTERISTICS:
        (A) LENGTH: 20 bases
        (B) TYPE: nucleic acid
        (C) STRANDEDNESS: single
        (D) TOPOLOGY: linear (ii) MOLECULE TYPE: DNA
```

(ix) FEATURE:
              (A) NAME/KEY:  CDS
              (B) LOCATION:  1..20
              (C) IDENTIFICATION METHOD:  E
              (D) OTHER INFORMATION:

(xi) SEQUENCE DESCRIPTION: SEQ ID NO:2:

CARGAYCARG CNAAYCCNGA                                                    20

(2) INFORMATION FOR SEQ ID NO:3:

(i) SEQUENCE CHARACTERISTICS:
              (A) LENGTH:  1782 base pairs
              (B) TYPE:  nucleic acid
              (C) STRANDEDNESS:  double
              (D) TOPOLOGY:  linear (ii) MOLECULE TYPE: Genomic DNA (vi) ORIGINAL SOURCE:
              (A) ORGANISM:  Porphyromonas (Bacteroides) gingivalis
              (B) STRAIN:  OMZ409

(ix) FEATURE:
              (A) NAME/KEY:  -35 signal
              (B) LOCATION:  9..14
              (C) IDENTIFICATION METHOD:  S
              (D) OTHER INFORMATION:

(ix) FEATURE:
              (A) NAME/KEY:  -10 signal
              (B) LOCATION:  32..37
              (C) IDENTIFICATION METHOD:  S
              (D) OTHER INFORMATION:

(ix) FEATURE:
              (A) NAME/KEY:  CDS
              (B) LOCATION:  60..1752
              (C) IDENTIFICATION METHOD:  S
              (D) OTHER INFORMATION:

(ix) FEATURE:
              (A) NAME/KEY:  Sig peptide
              (B) LOCATION:  60..105
              (C) IDENTIFICATION METHOD:  S
              (D) OTHER INFORMATION:

(ix) FEATURE:
              (A) NAME/KEY:  mat peptide
              (B) LOCATION:  208..1752
              (C) IDENTIFICATION METHOD:  E
              (D) OTHER INFORMATION:

(xi) SEQUENCE DESCRIPTION: SEQ ID NO:3:

AGTCTTTCTT TCGACGTTTT TAGAATCAAT TTAATATTAA TCCTTTTAAA CATTTGGCTT         60

ATG AAG TTA AAC AAA ATG TTT TTG GTC GGA GCA TTG CTC TCA TTG GGC         108

TTT GCT TCT TGT AGT AAA GAG GGC AAT GGC CCC GAT CCG GAC AAT GCG         156

GCG AAG TCG TAT ATG TCT ATG ACG TTG TCC ATG CCT ATG GGA AGT GCT         204

CGT GCG GGT GAC GGA CAG GAT CAA GCT AAC CCT GAT TAC CAT TAT GTA         252

GGA GAG TGG GCA GGA AAA GAC AAA ATT GAG AAA GTG AGC ATC TAC ATG         300

GTG CCT CAG GGT GGC CCT GGG CTT GTG GAG AGT GCT GAA GAT CTT GAT         348

TTT GGC ACT TAT TAT GAA AAT CCT ACT ATA GAT CCT GCA ACC CAC AAT         396

GCC ATT TTG AAA CCG AAA AAA GGT ATC AAG GTT AAT TCT GCT GTC GGC         444

AAG ACG GTT AAA GTA TAT GTG GTG CTC AAT GAC ATC GCC GGC AAG GCA         492

AAA GCC CTT TTG GCA AAT GTT AAT GCA GCA GAC TTT GAT GCT AAA TTC         540

AAA GAG GTA ATC GAA CTG TCT ACT CAG GCT CAG GCT TTA GGT ACG GTA         588

```
GCC GAT GGC CCG AAT CCT GCT ACA GCG GCT GGA AAG ATT GCC AAA AAG      636

AAT GGT ACT ACT GAT GAG ACA ATC ATG ATG ACC TGT TTG CAG CCT TCT      684

GAT GCT TTG ACT ATC GAA GCT GCT GTA TCC GAG GCC AAT GCT ATC GCA      732

GGG ATT AAG AAT CAG GCC AAG GTT ACG GTG GAG CGT TCT GTA GCA CGT      780

GCG ATG GTT TCA ACG AAA GCC CAG AGT TAT GAA ATT AAA GCC ACT ACT      828

CAA ATT GGA GAA ATT GCC GCA GGT TCT GTT TTG GCT ACC ATT ACG GAT      876

ATC AGA TGG GTT GTT GCT CAA GGA GAA CGT CGC CAA TAC CTA AGC AAG      924

AAA AGA GGA ACT GTT CCA GAA AAT ACT TGG GTT ACT CCG GGT TCT GGT      972

TTC GTT CCT ACC AGC AGC ACT TTC CAT ACA AAT GCT ACT GAG TAT TAT      1020

GAT TAT GCT GGT CTG TGG GAA GAT CAT AAT ACA AAT GAG GCC GTA ATC      1068

AGT GGA ACT CAA GTG CCG ACT TTG GCT GAT TAT CAG CTC CAG GAC GTG      1116

ACT GGC GAA TTG GCA AAT GCT CTT TCA GGG AAA TTC CTG CTG CCT AAT      1164

ACC CAT AAG TCA GGA GCT AAT GCT GCC TCG TCA GAC TAT AAG AGA GGT      1212

AAT ACT GCC TAT GTA TTA GTT CGT GCG AAG TTT ACT CCC AAG AAA GAA      1260

GCC TTT ATC GAT AGA GGT AAA ACT TAT TCA GAT AAT ACT GCA GTT CCT      1308

GAA TAT GTA GCA GGT GAA GAT TTC TTC GTT GGT GAG AAT GGC CAG TTC      1356

TAT GTG TCT ATG AAA TCC GTT ACA GAC CCC AAG GTA GGT GGT GTA GCT      1404

GGT ATG AAG GCA CAC AAA TAT GTG AAA GGC AAA GTA CTG TAC TAT GCT      1452

TGG TTG AAT CCC AGT ACT ACT TCT CCC GAT TCA TGG TGG AAT TCC CCT      1500

GTT GTG CGC AAC AAT ATC TAC CAT ATC CAC ATC AAG AGC ATC AAG AAG      1548

TTG GGC TTC AAC TGG AAT CCT TTG GTG CCG GAT CCG GAT CCT AGC AAC      1596

CCG GAA AAT CCG AAT AAC CCT GAC CCG AAT CCG GAT GAG CCG GGT ACT      1644

CCC GTT CCT ACA GAT CCC GAG CAA CCC CTA CCT GAT CAG GAT ACG TTC      1692

ATG TCG GTT GAG GTT ACA GTT TTG CCT TGG AAA GTT CAT TCC TAT GAG      1740

GTT GAT CTC TAA TTAGCTATTG TAAAATTTTC TTTTTGAGGG                     1782
```

DNA AND HOST CELLS ENCODING A CELL SURFACE PROTEIN OF PORPHYROMONAS GINGIVALIS

BACKGROUND OF THE INVENTION

1. Field of the Invention

This invention relates to a cell surface polypeptide of *Porphyromonas* (Bacteroides) *gingivalis* (another name; periodontopathic organism: hereinafter, referred to as *Porphyromonas gingivalis*) having a molecular weight of about 72-kDa (kilodalton) (hereinafter abbreviated as periodontopathic organism cell surface polypeptide), a DNA encoding the polypeptide, a recombinant DNA wherein the DNA is integrated and a microorganism containing the recombinant DNA.

The DNA obtained in the invention can be utilized as a reagent, namely as a probe for detecting *Porphyromonas gingivalis*. Further, the periodontopathic organism cell surface polypeptide obtained in the invention and produced by a microorganism can be utilized for a diagnosis of patients suffering with periodontal diseases and having antibodies against *Porphyromonas gingivalis*, as an antigen for preparing an antibody for diagnosing patients suffering with periodontal diseases and having *Porphyromonas gingivalis* or as a prophylactic vaccine for periodontal diseases.

2. Description of Related Art

It is reported by Yoshimura et al. in Infect. Immun., 57, 3646 (1989) that since the periodontopathic organism cell surface polypeptide exhibits strong immune response to the sera of patients of periodontal diseases, infecting with *Porphyromonas gingivalis*, antibodies against the polypeptide existing in the sera of the patients can be detected using it. Further, it is reported by Ogawa et al. in Nippon Saikin-gaku Zasshi, 44, 329 (1989), by Yoshimura et al. in J. Bacteriol., 160, 949 (1984) and by Yamaji et al. in Nisshishushi, 33, 349 (1991) that the immune response of the polypeptide is different from that of the known fimbrial protein from the known periodontopathic organism having a molecular weight of 41 kDa, and thus the periodontopathic organism cell surface polypeptide of the invention is different from the ciliary protein.

As to the structure of the periodontopathic organism cell surface polypeptide, its amino acid composition is reported by Yoshimura et al. in Infect. Immun. 57, 3646 (1989), and the amino-terminal amino acid sequence of a purified polypeptide thereof is reported by Yoshimura et al. in FEMS Microbiol. Lett., 92, 47 (1992). Elucidated amino acids are 40 amino acids, and when we compare 40 amino acid with an amino acid number estimated from the molecular weight of the periodontopathic organism cell surface polypeptide, the rate is only under 10%. Further, concerning with a DNA encoding the periodontopathic organism cell surface polypeptide, it is reported by Yoshimura et al. in FEMS Microbiol. Lett., 92, 47 (1992) that its part was obtained. However the base sequence of the gene is not elucidated at all.

The periodontopathic organism cell surface polypeptide is recovered from *Porphyromonas gingivalis* cells, but its supply amount is limited because of difficulty of the culture of *Porphyromonas gingivalis*. Thus development of an industrial process for supplying the periodontopathic organism cell surface polypeptide is desired.

SUMMARY OF THE INVENTION

According to the invention, there are provided a cell surface polypeptide of *Porphyromonas gingivalis* having an amino acid sequence shown in SEQ ID NO: 1 (Numbers 1–558), a DNA encoding the cell surface polypeptide of *Porphyromonas gingivalis* having the amino acid sequence shown in SEQ ID NO: 1 (Numbers 1–558), a recombinant DNA which is a DNA having integrated thereinto the DNA encoding the cell surface polypeptide of *Porphyromonas gingivalis* having the amino acid sequence shown in SEQ ID NO: 1 (Numbers 1–558), and a microorganism having the recombinant DNA which is the DNA having integrated thereinto the DNA encoding the cell surface polypeptide of *Porphyromonas gingivalis* having the amino acid sequence shown in SEQ ID No. 1 (Numbers 1–558).

Further, the DNAs encoding the cell surface polypeptide of *Porphyromonas gingivalis* having the amino acid sequence shown in SEQ ID NO: 1 (Numbers 1–558) according to the present invention include those wherein one or plural bases are added, deleted or replaced by site-directed mutagenesis (Nucleic Acid Research, 10, 6487–6508 (1982)). Therefore, a recombinant DNA wherein a DNA obtained by the mutagenesis is integrated, and a microorganism having the recombinant DNA are also included in the invention. Since a polypeptide produced by recombinant technique using a DNA wherein in the DNA encoding the cell surface polypeptide of *Porphyromonas gingivalis* having the amino acid sequence shown in SEQ ID NO: 1 (Numbers 1–558), one or plural bases are added, deleted or replaced, is a polypeptide wherein in the cell surface polypeptide of *Porphyromonas gingivalis* having the amino acid sequence shown in SEQ ID NO: 1 (Numbers 1–558), one or plural amino acids are added, deleted or replaced, this polypeptide is also included in the invention.

A DNA sequence encoding the amino acid sequence shown in SEQ ID No: 1 is shown in SEQ ID No: 3, wherein bases 76–1749 encodes amino acids 1–558.

BRIEF DESCRIPTION OF DRAWING

FIG. 1 is a drawing illustrating the process of creating a recombinant plasmid containing a DNA encoding the periodontopathic organism cell surface polypeptide.

DETAILED DESCRIPTION OF THE INVENTION

The DNA and recombinant DNA of the invention are prepared according to the following general process.

The whole DNA is prepared from *Porphyromonas gingivalis* according to the method of Meyer et al. (Cell, 30, 45 (1982)) and the method of Maniatis et al. (Molecular Cloning Laboratory Manual 2nd ed., Cold Spring Harbor Laboratory Press, published in 1989 (hereinafter referred to as Mol. clon.)), and the DNA is inserted into a vector DNA such as a plasmid DNA of *Escherichia coli* to give a library of recombinant DNAs. From the recombinant DNA library, a recombinant DNA having a DNA encoding the periodontopathic organism cell surface polypeptide is selected.

The culture broth of *Porphyromonas gingivalis* is centrifuged, the cells are collected, lysozyme, proteinase K and sodium dodecyl sulfate (SDS) are added thereto, and the cells are ruptured and dissolved. After phenol extraction, phenol-chloroform extraction and chloroform extraction, DNAs are recovered by ethanol precipitation.

The extracted DNAs are treated with 5 to 100 units/ml, preferably 10 units/ml of a restriction enzyme KpnI in a suitable solution, e.g. a solution containing 10 mM Tris-HCl buffer (e.g. pH 7.5), $MgCl_2$ (e.g. 6 mM) and NaCl (e.g. 10 mM), and then NaCl is added so as to be 100 mM and the DNA is treated with 5 to 100 units/ml, preferably 10 units/ml of a restriction enzyme XhoI. The DNAs after the treatment are fractionated using low melting point agarose gel electrophoresis (Lars Wieslander: Anal. Biochem., 98, 305 (1979)), and fragments of about 3.4 kilobases are recovered and integrated into a vector.

As the vector Blue-script, pUC18, pUC19, etc. can for example be used. When Blue-script is used, the vector DNA is treated with 5 to 100 units/ml, preferably 10 units/ml of a restriction enzyme KpnI in a suitable solution, e.g. a solution containing 10 mM Tris-HCl buffer (e.g. pH 7.5), $MgCl_2$ (e.g. 6 mM) and NaCl (e.g. 10 mM), and then NaCl is added so as to be 100 mM and the DNA is treated with 5 to 100 units/ml, preferably 10 units/ml of a restriction enzyme XhoI to cleave the KpnI and XhoI sites of the vector DNA. These DNAs are fractionated using low melting point agarose gel electrophoresis (Lars Wieslander: Anal. Biochem., 98, 305 (1979)), and a fragment of about 2.9 kilobases is recovered.

This vector DNA fragment and the previously prepared DNA fragments are incubated for a definite time (e.g. 2 hours) at an appropriate temperature (e.g. 16° C.) using a DNA ligation kit (produced by Takara Shuzo Co.). Thus recombinant DNAs are obtained.

Using the obtained recombinant DNA, *Escherichia coli*, for example an XL1-Blue strain, an LE 392 strain, DH 5 strain or a JM 83 strain is transformed, for example according to the method of Scott et al. (Katsuya Shigesada: Saibo Kogaku, 2, 616 (1983)). When Blue-script is used as the vector, since the ampicillin-resistant gene exists on the recombinant DNAs, the transformed *Escherichia coli* strains exhibit ampicillin resistance. Hereinafter, a method for selecting a strain having a novel recombinant DNA carrying the periodontopathic organism cell surface polypeptide gene from the ampicillin-resistant ($Ap^r$) transformants is described. Namely, the obtained recombinant DNAs are fixated on a nitrocellulose filter, and associated with a synthetic DNA probe having a DNA sequence estimated from the amino acid sequence of the periodontopathic organism cell surface polypeptide, and ones strongly associating therewith are selected (the method of Grunstein-Hogness, Proc. Natl. Acad. Sci. U.S.A., 72, 3961 (1975)). The probe DNA is synthesized by a usual triester method (J. Am. Chem. Soc., 97, 7327 (1975)). The selection with the synthetic DNA probe can further be ascertained according to the method of Southern et al. (J. Mol. Biol., 98, 503 (1975)), and by this method a recombinant DNA having the DNA fragment encoding periodontopathic organism cell surface polypeptide can be identified.

An example of the thus obtained recombinant DNAs is a plasmid pCSP 409. This plasmid can be used as a supply source of the DNA encoding the periodontopathic organism cell surface polypeptide.

Further, a DNA encoding the periodontopathic organism cell surface polypeptide is cut out from the novel recombinant DNA of the invention, the DNA is integrated into an expression vector DNA, the resultant recombinant DNA is introduced into a microorganism, the resultant transformed microorganism is cultured to form and accumulate the periodontopathic organism cell surface polypeptide in the culture broth, and the polypeptide is recovered. Thereby the polypeptide can be prepared.

As the recombinant DNA containing the DNA encoding the periodontopathic organism cell surface polypeptide, the above plasmid pCSP 409 can be mentioned as a suitable example. As the expressing vector DNA, any one can be used so long as it can express the inserted DNA in the microorganism. Preferably, there can be used a vector DNA which has a suitable promoter, e.g. the promoter of the tryptophan (trp) system, the lactose (lac) system, the PL system or the like, into the downstream of which a DNA can be inserted, and further wherein the interval between the contained Shine-Dalgarno sequence (hereinafter abbreviated as SD sequence) and the translation initiation codon (ATG) is adjusted to a suitable distance, e.g. 6 to 18 base pairs. As a specifically preferred vector DNA, plasmid pGEL1 can be mentioned. An *Escherichia coli* containing pGEL1 is deposited with National Institute of Bioscience and Human Technology, Agency of Industrial Science and Technology (Bikoken) on Oct. 6, 1984 as *Escherichia coli* IGEL1 (FERM BP-629).

Recombination between the DNA encoding the polypeptide and the vector DNA can be conducted by a method described in Mol. clon., namely using a general recombinant DNA method to digest both DNAs with a restriction enzyme and conduct ligation with T4DNA ligase. Purification of DNA fragments formed by the restriction enzyme digestion is conducted by low melting point agarose gel electrophoresis (L. Wieslander: Anal. Biochem., 98, 305 (1979), hereinafter referred to as LGT method), etc. The ligation reaction of the DNA fragments is conducted at 5 to 25° C., preferably 16° C. for 15 minutes to 16 hours, using a DNA ligation kit (produced by Takara Shuzo Co.), or at 1 to 37° C. (preferably 3 to 20° C.) for 15 minutes to 72 hours (preferably 2 to 20 hours) in a reaction solution containing 2 to 200 mM (preferably 10 to 40 mM) of Tris-HCl (pH 6.1 to 9.5, preferably pH 7.0 to 8.0), 2 to 20 mM (preferably 5 to 10 mM) of $MgCl_2$, 0.1 to 10 mM (preferably 0.5 to 2.0 mM) of ATP and 1 to 50 mM (preferably 5 to 10 mM) of dithiothreitol, using 0.3 to 10 units of T4DNA ligase.

The resultant recombinant DNA is introduced into a microorganism, if necessary using the transformation method of Cohen et al. (S. N. Cohen et al.: Proc. Natl. Acad. Sci. U.S.A., 69, 2110 (1972)). As the microorganism, any one can be used so long as it can express the DNA encoding the periodontopathic organism cell surface polypeptide of the invention, and form and accumulate the polypeptide in the culture broth. Preferably used is *Escherichia coli*.

Isolation of the DNA encoding the periodontopathic organism cell surface polypeptide from the *Escherichia coli* having the recombinant DNA for determining the base sequence of the DNA is conducted using the method of Birnboim et al. (H. C. Birnboim et al.: Nucleic Acids Res., 7, 1513 (1979)), etc.

The isolated recombinant DNA is digested with 1 to 10 kinds of restriction enzymes and then treated by agarose gel electrophoresis or polyacrylamide gel electrophoresis, and the cleavage sites are checked. The base sequence of the DNAs is determined according to Maxam-Gilbert method (Proc. Natl. Acad. Sci., 74, 560 (1977)) or Sanger method using M13 phage (Sanger et al., Proc. Natl. Acad. Sci. U.S.A., 74, 5463 (1977); Amersham Co., M13 Cloning and Sequencing Handbook).

Preparation of the periodontopathic organism cell surface polypeptide from the microorganism having the recombinant DNA wherein the DNA encoding the cell surface polypeptide of *Porphyromonas gingivalis* is integrated can be conducted by culturing the microorganism in a medium, and recovering and purifying the polypeptide accumulated in the culture broth or in the cells.

As the medium, any one can be used so long as it is suitable for the groth of the microorganism and the production of the periodontopathic organism cell surface polypeptide, and synthetic media, natural media, etc. are used.

There can be used as carbon sources glucose, fructose, lactose, glycerol, mannitol, sorbitol, etc., as nitrogen sources ammonium chloride, ammonium sulfate, Casamino acid, yeast extract, polypeptone, meat extract, Bacto-tryptone, etc., as other nutrients potassium dihydrogenphosphate, dipotassium hydrogenphosphate, sodium chloride, magnesium sulfate, vitamin $B_1$, magnesium chloride, etc.

Culture is conducted at a pH of 5.5 to 8.5 and a temperature of 18 to 40° C. preferably by stirring culture. After the start of the culture, the periodontopathic organism cell surface polypeptide is accumulated in 5 to 90 hours. When a microorganism such as *Escherichia coli* accumulating the polypeptide intracellularly is used, the cells are collected from the culture broth by centrifugation, etc. and ruptured by ultrasonic treatment, etc. to give an extract. When a microorganism secreting the periodontopathic organism cell surface polypeptide extracellularly is used, the culture broth is used as an extract.

Purification of the periodontopathic organism cell surface polypeptide from the extract can be conducted according to fractionation with a base or solvent, ion exchange chromatography, gel filtration, affinity chromatography, etc.

Detection of the resultant periodontopathic organism cell surface polypeptide can be conducted according to immunoassay, particularly using Western blot technique (Proc. Natl. Acad. Sci. U.S.A., 76, 4350 (1979)), etc.

Examples of the invention are set forth below.

EXAMPLE 1

(1) Preparation of the Genomic DNA from *Porphyromonas gingivalis*

The genomic DNA was prepared as follows from *Porphyromonas gingivalis* according to the method of Meyer et al. (Cell, 30, 45 (1982)). The cells of *Porphyromonas gingivalis* (5 g) (wet weight) was suspended in 10 ml of 50 mM Tris-HCl (pH 7.5) containing 50 mM EDTA and 50 mM NaCl, 2 mg/ml of lysozyme was added, incubation was conducted at 37° C. for 10 minutes, 0.5 mg/ml of proteinase K and 1.5% of SDS were added, and incubation was conducted at 50° C. for 6 hours to solubilize the cells. An equal amount of a phenol solution was added to this homogenate and extraction was conducted three times, and then extraction was conducted twice with phenol-chloroform and further once with chloroform. After the extraction, DNA was recovered by ethanol precipitation. The DNA precipitate was dissolved in 2 ml of a Tris-HCl (pH 8.0) solution containing 1 mM EDTA, 2 µg/ml of RNase was added, and incubation was conducted at 65° C. for 4 hours. Then, 200 µl of 3M sodium acetate solution and further equal amount of isopropyl alcohol were added and the deposited DNA was recovered by centrifugation. The resultant DNA (about 10 mg) was dissolved in 1 ml of a solution consisting of 10 mM Tris-HCl (pH 8.0) and 1 mM EDTA.

(2) Insertion of the plasmid of *Porphyromonas gingivalis* into a Vector

Creation of a recombinant DNA was conducted according to Mol. clon. The outline of the steps was shown in FIG. 1. The above genomic DNA of *Porphyromonas gingivalis* (300 µg) was added to 300 µl of a solution consisting of 10 mM Tris-HCl (pH 7.5), 6 mM $MgCl_2$ and 10 mM NaCl, 500 units of KpnI (produced by Takara Shuzo Co., hereinafter all restriction enzymes are produced by Takara Shuzo Co. unless otherwise noted) was added, and reaction was conducted at 37° C. for 6 hours. Then, NaCl was added so as to be 100 mM, 500 units of XhoI was added and reaction was conducted at 37° C. for 3 hours. About 50 µg of fragments each of about 3.4 kb were obtained from this reaction solution according to LGT method. Further, 10 µg of a vector plasmid (Bluescript) DNA was added to 30 µl of a solution consisting of 10 mM Tris-HCl (pH 7.5), 6 mM $MgCl_2$ and 10 mM NaCl, 50 units of KpnI was added, and reaction was conducted at 37° C. for 6 hours. Then, NaCl was added so as to be 100 mM, 50 units of XhoI was added and reaction was conducted at 37° C. for 3 hours. About 5 µg of a fragment of about 2.9 kb was obtained from this reaction solution according to LGT method. This fragment was mixed with 30 µg of the genomic DNA of *Porphyromonas gingivalis* treated with the restriction enzymes and incubation was conducted at 16° C. for 2 hours using a DNA ligation kit (produced by Takara Shuzo Co.) to give recombinant DNAs containing the genomic DNAs of *Porphyromonas gingivalis*.

(3) Selection of Recombinant DNAs containing the DNA Encoding the Periodontopathic Organism Cell Surface Polypeptide An *Escherichia coli* strain XL1-Blue (STRATAGENE Co.) was transformed according to the method of Scott et al. (Katsuya Shigesada: Saibo Kogaku, 2, 616 (1983)) using the recombinant DNA obtained in Example 2. The resultant about 10,000 colonies were fixated on nitrocellulose. A synthetic DNA represented by the following formula (SEQ ID NO: 2) corresponding to the sequence of 7 amino acids at the N-terminal site of the purified cell surface polypeptide Formula CARGAYCARG CNAAYCCNGA 20 

(wherein the base symbols are based on the guideline for preparation of a specification containing base sequences or amino acid sequences) was labeled with digoxigenin (hereinafter referred to as DIG) at the 3'-terminus, using DIG Oligonucleotide 3'-End Labeling Kit, BOEHRINGER MANNHEIM GmbH according to the operation method in the attached manual. Thus, 3 strains wherein strong association with the DIG-labeled probe was observed at 40° C. were selected (the method of Grunstein-Hogness, Proc. Natl. Acad. Sci. U.S.A., 72, 3961 (1975)). On the obtained 3 strains, association with the above probe was ascertained according to the method of Southern (J. Mol. Biol., 98, 503 (1975)). These plasmids were designated pCSP409-A, B and C, and all of them were thought to contain a DNA encoding the periodontopathic organism cell surface polypeptide because they have the DNA sequence expected from the amino acid sequence of the purified periodontopathic organism cell surface polypeptide.

The above pCSP409-A is hereinafter called pCSP409, and the whole nucleotide sequence of its translation region was determined according to Sanger method using M13 phage (Sanger et al., Proc. Natl. Acad. Sci. U.S.A., 74, 5463 (1977): Amersham Co. M13 Cloning and Sequence Handbook)). Thus revealed base sequence and the amino acid sequence determined therefrom are shown in SEQ ID NO: 1.

The *Escherichia coli* containing the recombinant plasmid wherein pCSP409 was integrated was deposited with the National Institute of Bioscience and Human Technology, Agency of Industrial Science and Technology, 1–3, Higashi 1-chome, Tsukuba-shi, Ibarakiken, 305 Japan, Bikoken on Mar. 23, 1994 as *Escherichia coli* CSP409 (accession number FERM BP-4614).

(4) Production of the Periodontopathic Organism Cell Surface Polypeptide from *Escherichia coli* CSP409

*Escherichia coli* CSP409 obtained in (3) was inoculated in 10 ml of MCG medium (containing 0.6% disodium hydrogenphosphate, 0.3% potassium dihydrogenphosphate, 0.5% sodium chloride, 0.1% ammonium chloride, 0.5% glucose, 0.5% Casamino acid, 1 mM magnesium sulfate and 4 μg/ml vitamin $B_1$, pH 7.2), and cultured at 30° C. for 7 hours. The resultant culture broth was inoculated in 50 ml of MCG medium and cultured at 30° C. for 5 hours.

The cells were recovered from the culture broth by centrifugation (CR-20 produced by Hitachi, Ltd., Rotor RPR16-516; 8,000 rpm, 10 minutes). The resultant cells was dissolved in the buffer of Remuli (pH 7.4; Nature, 227, 680 (1970)), and assay was conducted according to Western blot technique (Proc. Natl. Acad. Sci. U.S.A., 76, 4350 (1979)) using the serum of a patient suffering with a periodontal disease and the serum of a normal subject. As a result, a band exhibiting the periodontopathic organism cell surface polypeptide specific to the serum of a patient suffering with a periodontal disease was observed.

By a microorganism containing a recombinant DNA wherein a DNA encoding the periodontopathic organism cell surface polypeptide of *Porphyromonas gingivalis* of the invention was integrated, the cell surface polypeptide of a periodontopathic organism useful for prophylaxis and diagnosis of periodontal diseases can be obtained in a large amount. Therefore, the invention can be utilized in diagnostic medicament, prophylactic vaccine, etc. of periodontal diseases.

We claim:

1. An isolated DNA encoding a cell surface polypeptide of *Porphyromonas gingivalis* comprising the amino acid sequence shown in SEQ ID NO: 1.

2. The isolated DNA according to claim 1, comprising the nucleic acid sequence shown in SEQ ID NO: 3.

3. A recombinant DNA comprising the DNA according to claim 1.

4. The recombinant DNA according to claim 3, wherein the recombinant DNA is plasmid pCSP409.

5. A microorganism containing a recombinant DNA comprising a DNA encoding a cell surface polypeptide of *Porphyromonas gingivalis* comprising the amino acid sequence shown in SEQ ID NO: 1.

6. The microorganism according to claim 5, wherein the DNA comprises the nucleic acid sequence shown in SEQ ID NO: 3.

7. The microorganism according to claim 5, wherein the microorganism is *Escherichia coli*.

8. The microorganism according to claim 7, which is *Escherichia coli* CSP409 deposited under accession number FERM BP-467.

9. A purified cell surface polypeptide of *Porphyromonas gingivalis* comprising the amino acid sequence shown in SEQ ID NO: 1.

10. The purified cell surface polypeptide according to claim 9, which is encoded by the nucleic acid sequence shown in SEQ ID NO: 3.

11. A method for producing a cell surface polypeptide of *Porphyromonas gingivalis*, which comprises culturing a microorganism containing a recombinant DNA comprising a DNA encoding a cell surface polypeptide of *Porphyromonas gingivalis* having the amino acid sequence shown in SEQ ID NO: 1 under conditions suitable for expressing the cell surface polypeptide.

12. The method according to claim 11, wherein the recombinant DNA comprises the nucleic acid sequence shown in SEQ ID NO: 3.

13. The method according to claim 11, wherein the recombinant DNA is plasmid pCSP409.

14. The method according to claim 11, wherein the microorganism is *Escherichia coli*.

15. The method according to claim 11, wherein the microorganism is *Escherichia coli* CSP409.

* * * * *